US00PP19195P2

(12) United States Plant Patent
Hofmann et al.

(10) Patent No.: US PP19,195 P2
(45) Date of Patent: Sep. 9, 2008

(54) ***NEMESIA* PLANT NAMED 'INUPPEAR'**

(50) Latin Name: *Nemesia hybrida*
Varietal Denomination: Inuppear

(75) Inventors: Silva Hofmann, Mainz (DE); Hendrik Theobald, Heidesheim (DE)

(73) Assignee: Innovaplant GmbH & Co KG, Gensingen (DE)

( * ) Notice: Subject to any disclaimer, the term of this patent is extended or adjusted under 35 U.S.C. 154(b) by 0 days.

(21) Appl. No.: 11/800,795

(22) Filed: May 7, 2007

(51) Int. Cl.
*A01H 5/00* (2006.01)

(52) U.S. Cl. ..... Plt./458
(58) Field of Classification Search ..... Plt./458, Plt./263
See application file for complete search history.

*Primary Examiner*—Kent L. Bell
*Assistant Examiner*—S. B. McCormick-Ewoldt
(74) *Attorney, Agent, or Firm*—C. A. Whealy

(57) ABSTRACT

A new and distinct cultivar of *Nemesia* plant named 'Inuppear', characterized by its compact, upright and rounded growth habit; early flowering habit; freely flowering habit; white-colored flowers with orange-colored centers; and tolerance to low temperatures.

1 Drawing Sheet

Botanical designation: *Nemesia hybrida.*
Cultivar denomination: 'Inuppear'.

BACKGROUND OF THE INVENTION

The present invention relates to a new and distinct cultivar of *Nemesia,* botanically known *Nemesia hybrida* and hereinafter referred to by the name 'Inuppear'.

The new *Nemesia* is a naturally-occurring whole plant mutation of the *Nemesia hybrida* Inuprasp, disclosed in U.S. Plant Pat. No. 17,978. The new *Nemesia* was discovered and selected by the Inventors as a single flowering plant within a population of plants of the cultivar Inuprasp in a controlled environment in Gensingen, Germany during the summer of 2004.

Asexual reproduction of the new *Nemesia* by terminal cuttings in a controlled environment in Gensingen, Germany since the summer of 2004, has shown that the unique features of this new *Nemesia* are stable and reproduced true to type in successive generations.

SUMMARY OF THE INVENTION

The cultivar Inuppear has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Inuppear'. These characteristics in combination distinguish 'Inuppear' as a new and distinct cultivar of *Nemesia:*

1. Compact, upright and rounded growth habit.
2. Early flowering habit.
3. Freely flowering habit.
4. White-colored flowers with orange-colored centers.
5. Tolerant to low temperatures.

Plants of the new *Nemesia* differ from plants of the parent, the cultivar Inuprasp primarily in flower color as plants of the cultivar Inuprasp have pink-colored flowers.

Plants of the new *Nemesia* can be compared to plants of the cultivar Improved Innocence, not patented. In side-by-side comparisons conducted by the Inventors in Gensingen, Germany, plants of the new *Nemesia* differed from plants of the cultivar Improved Innocence in the following characteristics:

1. Plants of the new *Nemesia* were more vigorous and stronger than plants of the cultivar Improved Innocence.
2. Plants of the new *Nemesia* had larger flowers than plants of the cultivar Improved Innocence.

BRIEF DESCRIPTION OF THE PHOTOGRAPHS

The accompanying colored photographs illustrate the overall appearance of the new *Nemesia,* showing the colors as true as it is reasonably possible to obtain in colored reproductions of this type. Colors in the photographs may differ slightly from the color values cited in the detailed botanical description which accurately describe the colors of the new *Nemesia.*

The photograph at the bottom of the sheet comprises a side perspective view of a typical flowering plant of 'Inuppear' grown in a container.

The photograph at the top of the sheet is a close-up view of typical flowers of 'Inuppear'.

DETAILED BOTANICAL DESCRIPTION

The aforementioned photographs and following observations, measurements and values describe plants grown in Bonsall, Calif. in containers in an outdoor nursery during the winter and under conditions which closely approximate commercial production. During the production of the plants, day temperatures range from about 18° C. to 32° C. and night temperatures range from about 16° C. to 24° C. Plants were pinched one time and were about ten weeks old when the photographs and the description were taken. In the description, color references are made to The Royal Horticultural Society Colour Chart, 1995 Edition, except where general terms of ordinary dictionary significance are used.

Botanical classification: *Nemesia hybrida* cultivar Inuppear.

Parentage: Naturally-occurring whole plant mutation of the *Nemesia hybrida* Inuprasp, disclosed in U.S. Plant Pat. No. 17,978.

Propagation:

*Type.*—By terminal cuttings.

*Time to initiate roots, summer.*—About five days at 25° C.

*Time to initiate roots, winter.*—About ten days at 16° C.

*Time to produce a rooted young plant, summer.*—About ten days at 25° C.

*Time to produce a rooted young plant, winter.*—About two weeks at 16° C.

*Root description.*—Fine; white in color.

*Rooting habit.*—Freely branching.

Plant description:

*Plant and growth habit.*—Compact, upright and rounded growth habit. Moderately vigorous growth habit. Freely branching; about five to six primary branches develop per plant with numerous secondary laterals.

*Plant height.*—About 30 cm.

*Plant diameter.*—About 24 cm.

Lateral branch description:

*Length.*—About 28 cm.

*Diameter.*—About 3 mm.

*Internode length.*—About 1.7 cm.

*Strength.*—Strong.

*Aspect.*—Mostly upright.

*Texture.*—Smooth, glabrous.

*Color.*—146B.

Foliage description:

*Arrangement.*—Opposite, simple.

*Length.*—About 3.6 cm.

*Width.*—About 1.7 cm.

*Shape.*—Lanceolate.

*Apex.*—Acute.

*Base.*—Attenuate.

*Margin.*—Serrate.

*Texture, upper and lower surfaces.*—Smooth, glabrous.

*Venation pattern.*—Pinnate; arcuate.

*Color.*—Developing foliage, upper surface: 137C. Developing foliage, lower surface: 144A. Fully expanded foliage, upper surface: 137B; venation, 137C. Fully expanded foliage, lower surface: 146B; venation, 146B.

*Petiole length.*—About 7 mm.

*Petiole diameter.*—About 3 mm.

*Petiole texture, upper and lower surfaces.*—Smooth, glabrous.

*Petiole color, upper and lower surfaces.*—144A.

Flower description:

*Flower arrangement and habit.*—Zygomorphic solitary flowers arranged on terminal racemes; flowering acropetally towards the apex. Flowers bilabiate. Flowers face upright to outwardly. Flowers last about four to five days on the plant. Flowers not persistent. Freely flowering habit with about 24 flowers and flower buds per inflorescence.

*Fragrance.*—Faint; sweet, spicy.

*Natural flowering season.*—In Germany, plants flower from May through September; flowering continuous during this period.

*Inflorescence height.*—About 7.5 cm to 8 cm.

*Inflorescence diameter.*—About 5 cm.

*Flower diameter.*—About 2.3 cm.

*Flower length.*—About 1.8 cm.

*Flower depth.*—About 1.7 cm.

*Flower buds.*—Length: About 1.2 cm. Diameter: About 1.1 cm. Shape: Oval. Color: 157A.

*Petals.*—Arrangement: Five petals; four upper petals fused at base to form an upright lobed and arched upper or banner lip; lower petal modified into a large lip with convex oval protuberance and nectar spur. Shape: Oval to rounded. Apex: Rounded. Margin: Praemorse. Length: Center upper petals: About 1.1 cm. Lateral upper petals: About 8 mm. Lower petal: About 1 cm. Width: Center upper petals: About 8 mm. Lateral upper petals: About 8 mm. Lower petal: About 2 cm. Texture, upper and lower surfaces: Smooth, glabrous. Color: When opening, upper surface: Close to 155A. When opening, lower surface: Close to 157B. Fully opened, upper surface: Close to 155A; protuberance, close to 17A; thin streaks at base of upper petals, 93B. Fully opened, lower surface: Close to 155D; nectar spur, close to 157B.

*Sepals.*—Arrangement: Calyx star-shaped with five sepals fused at the base. Shape: Elliptic. Apex: Acute. Margin: Entire. Length: About 4 mm. Width: About 2.5 mm. Texture, upper and lower surfaces: Pubescent. Color, upper surface: 146B. Color, lower surface: 146A.

*Peduncles.*—Length: About 3.5 cm to 4 cm. Diameter: About 2 mm. Angle: Mostly erect. Strength: Strong. Texture: Pubescent. Color: 137B.

*Pedicels.*—Length: About 1.2 cm. Diameter: About 1 mm. Angle: About 45° to 60° from peduncle axis. Strength: Strong. Texture: Pubescent. Color: 144A.

*Reproductive organs.*—Stamens: Quantity/arrangement: Four per flower. Filament length: About 3 mm. Filament color: Close to 155D. Anther shape: Oval. Anther length: Less than 1 mm. Anther color: 13A. Pollen amount: Scarce. Pollen color: 13B. Pistils: Quantity: One per flower. Pistil length: About 2.5 mm. Style length: About 1 mm. Style color: 145C. Stigma shape: Rounded. Stigma color: 145B. Ovary color: 146C. Seed/fruit: Seed and fruit development have not been observed on plants of the new *Nemesia*.

Pathogen/pest resistance: Plants of the new *Nemesia* have not been observed to be resistant to pests and pathogens common to *Nemesia*.

Garden performance: Plants of the new *Nemesia* have been observed to tolerate wind and rain and have good garden performance.

Temperature tolerance: Plants of the new *Nemesia* have been observed to tolerate temperatures from about 0° C. to about 35° C.

It is claimed:

1. A new and distinct *Nemesia* plant named 'Inuppear' as illustrated and described.

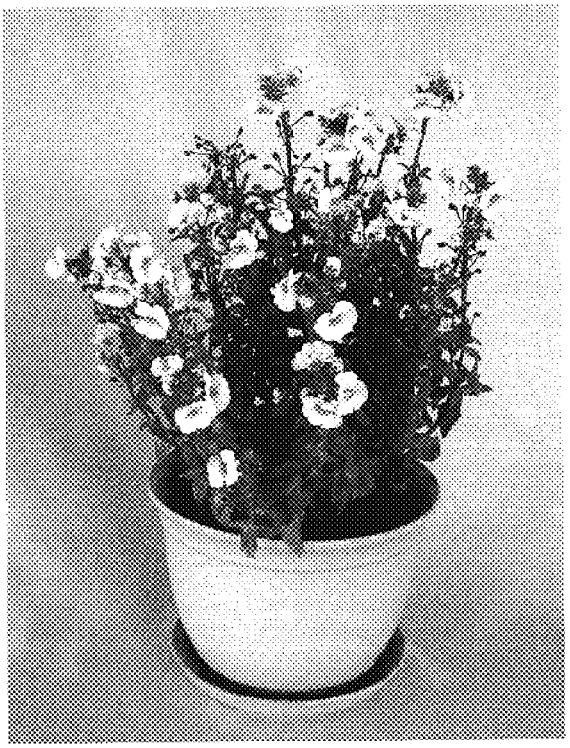
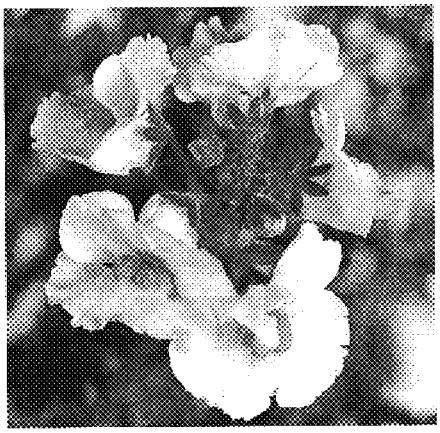

* * * * *